(12) United States Patent
Sánchez Vives et al.

(10) Patent No.: US 10,835,707 B2
(45) Date of Patent: Nov. 17, 2020

(54) PHYSIOLOGICAL RESPONSE

(71) Applicants: UNIVERSITAT DE BARCELONA, Barcelona (ES); INSTITUCIÓ CATALANA DE RECERCA I ESTUDIS AVANÇATS, Barcelona (ES); INSTITUT D'INVESTIGACIONS BIOMÈDIQUES AUGUST PI I SUNYER (IDIBAPS), Barcelona (ES)

(72) Inventors: Mavi Sánchez Vives, Barcelona (ES); Mel Slater, Barcelona (ES); Jorge Arroyo Palacios, Barcelona (ES)

(73) Assignees: UNIVERSITAT DE BARCELONA, Barcelona (ES); INSTITUCIÓ CATALANA DE RECERCA I ESTUDIS AVANÇATS, Barcelona (ES); INSTITUT D'INVESTIGACIONS BIOMÈDIQUES AUGUST PI I SUNYER (IDIBAPS), Barcelona (ES)

( * ) Notice: Subject to any disclaimer, the term of this patent is extended or adjusted under 35 U.S.C. 154(b) by 298 days.

(21) Appl. No.: 15/883,692

(22) Filed: Jan. 30, 2018

(65) Prior Publication Data

US 2018/0154106 A1 Jun. 7, 2018

Related U.S. Application Data

(63) Continuation of application No. PCT/EP2016/068205, filed on Jul. 29, 2016.

(30) Foreign Application Priority Data

Jul. 31, 2015 (EP) .................................... 15382405

(51) Int. Cl.
*A61M 21/02* (2006.01)
*A61B 5/16* (2006.01)
(Continued)

(52) U.S. Cl.
CPC ............ *A61M 21/02* (2013.01); *A61B 5/1114* (2013.01); *A61B 5/16* (2013.01); *A61B 5/6814* (2013.01);
(Continued)

(58) Field of Classification Search
CPC ......... A61B 5/744; A61B 5/16; A61B 5/6814; A61B 5/1114; A61M 2209/088;
(Continued)

(56) References Cited

U.S. PATENT DOCUMENTS 5,800,337 A * 9/1998 Gavish ................. A61B 5/1135
600/27
6,026,322 A * 2/2000 Korenman ........... A61B 5/0017
600/547

(Continued)

FOREIGN PATENT DOCUMENTS

WO 2009147625 A1 12/2009

OTHER PUBLICATIONS

Perez-Marcos et al., A Fully Immersive Set-Up for Remote Interaction and Neurorehabilitation Based on Virtual Body Ownership, Frontiers in Neurology, Methods Article, Jul. 10, 2012, vol. 3, Article 110, pp. 1-9.

(Continued)

*Primary Examiner* — Navin Natnithithadha
*Assistant Examiner* — Sunita Reddy
(74) *Attorney, Agent, or Firm* — Edell, Shapiro & Finnan, LLC

(57) ABSTRACT

Methods for provoking a physiological response in a subject comprising: receiving from sensors an orientation of an HMD of the subject and a parameter indicative of a physiological state of the subject, determining a video signal representing an avatar of the subject in a virtual reality scenario to be displayed on the head mounted display taking (Continued)

into account the orientation of the head mounted display, wherein the video signal includes an indication of a physiological state of the avatar, and sending the video signal to the head mounted display for visualization, optionally accompanied by a suitable audio signal. During a first period, the indication of the physiological state of the avatar substantially corresponds to the measured physiological state, and during a second period the indication of the physiological state of the avatar does not correspond to the measured physiological state. Related computer program and computing systems are also disclosed.

18 Claims, 2 Drawing Sheets

(51) Int. Cl.
<table>
<tr><td>G06F 3/01</td><td>(2006.01)</td></tr>
<tr><td>A61B 5/00</td><td>(2006.01)</td></tr>
<tr><td>A61B 5/11</td><td>(2006.01)</td></tr>
<tr><td>A61M 21/00</td><td>(2006.01)</td></tr>
<tr><td>G06T 13/40</td><td>(2011.01)</td></tr>
</table>

(52) U.S. Cl.
CPC .............. *A61B 5/744* (2013.01); *G06F 3/012* (2013.01); *G06F 3/016* (2013.01); *A61M 2021/005* (2013.01); *A61M 2021/0027* (2013.01); *A61M 2205/50* (2013.01); *A61M 2205/582* (2013.01); *A61M 2209/088* (2013.01); *A61M 2230/06* (2013.01); *A61M 2230/42* (2013.01); *A61M 2230/50* (2013.01); *A61M 2230/63* (2013.01); *A61M 2230/65* (2013.01); *G06T 13/40* (2013.01)

(58) Field of Classification Search
CPC .......... A61M 2230/65; A61M 2230/63; A61M 2230/50; A61M 2230/42; A61M 2230/06; A61M 2205/582; A61M 2205/50; A61M 2021/005; A61M 2021/0027; A61M 21/02; G06F 3/012; G06F 3/016; G06T 13/40

USPC ............................... 600/26–28; 128/897–899
See application file for complete search history.

(56) References Cited

U.S. PATENT DOCUMENTS

<table>
<tr><td>2005/0154264 A1*</td><td>7/2005</td><td>Lecompte</td><td>A61B 5/486<br>600/300</td></tr>
<tr><td>2008/0012701 A1*</td><td>1/2008</td><td>Kass</td><td>A61B 5/0002<br>340/539.11</td></tr>
<tr><td>2009/0040231 A1</td><td>2/2009</td><td>Sano et al.</td><td></td></tr>
<tr><td>2010/0062403 A1*</td><td>3/2010</td><td>Williams</td><td>G09B 7/02<br>434/185</td></tr>
<tr><td>2011/0270135 A1</td><td>3/2011</td><td>Dooley et al.</td><td></td></tr>
<tr><td>2011/0172500 A1*</td><td>7/2011</td><td>Van Dooren</td><td>A61B 5/486<br>600/300</td></tr>
<tr><td>2011/0213197 A1*</td><td>9/2011</td><td>Robertson</td><td>G16H 50/50<br>600/27</td></tr>
<tr><td>2013/0083009 A1</td><td>4/2013</td><td>Geisner et al.</td><td></td></tr>
<tr><td>2014/0139551 A1</td><td>5/2014</td><td>McCulloch et al.</td><td></td></tr>
<tr><td>2014/0316192 A1*</td><td>10/2014</td><td>de Zambotti</td><td>A61M 21/02<br>600/28</td></tr>
<tr><td>2014/0350431 A1*</td><td>11/2014</td><td>Hagedorn</td><td>A61B 5/0478<br>600/544</td></tr>
<tr><td>2015/0099946 A1*</td><td>4/2015</td><td>Sahin</td><td>A61B 5/16<br>600/301</td></tr>
<tr><td>2016/0005320 A1*</td><td>1/2016</td><td>deCharms</td><td>G09B 5/065<br>434/236</td></tr>
<tr><td>2016/0034764 A1*</td><td>2/2016</td><td>Connor</td><td>G06K 9/00771<br>348/158</td></tr>
<tr><td>2016/0317383 A1*</td><td>11/2016</td><td>Stanfield</td><td>A61N 1/36014</td></tr>
<tr><td>2017/0039045 A1*</td><td>2/2017</td><td>Abrahami</td><td>A61B 5/0205</td></tr>
<tr><td>2018/0081439 A1*</td><td>3/2018</td><td>Daniels</td><td>G06F 3/011</td></tr>
<tr><td>2020/0086078 A1*</td><td>3/2020</td><td>Poltorak</td><td>A61B 5/4809</td></tr>
</table>

OTHER PUBLICATIONS

International Search Report in corresponding PCT Application No. PCT/EP2016/068205, dated Oct. 20, 2016.

* cited by examiner

PHYSIOLOGICAL RESPONSE

CROSS-REFERENCE TO RELATED APPLICATIONS

This application relates to and claims the benefit and priority to International Application No. PCT/EP2016/068205, filed Jul. 29, 2016, which claims the benefit and priority to European Patent Application No. 15382405.7 filed Jul. 31, 2015.

TECHNICAL FIELD

The present disclosure relates to methods and systems for provoking a physiological response of a subject. It further relates to methods and systems and computer readable media for behavior therapy of a subject.

BACKGROUND

A mental disorder, also called a mental illness or psychiatric disorder, is a mental or behavioral pattern or anomaly that causes either suffering or an impaired ability to function in ordinary life, and which is not a developmental or social norm. Mental disorders are generally defined by a combination of how a person feels, acts, thinks or perceives. This may be associated with particular regions or functions of the brain or the rest of the nervous system, often in a social context. There are many different categories of mental disorders, for example anxiety or fear disorders. The most usual treatments and support for mental disorders comprise psychotherapy and/or medication. However, such methods are not always effective in the short or the long term, they are costly, and require the individual to be actively involved and proactive in order to make the most of the methods. For instance, the patient needs to take medication regularly, assist therapy sessions and be emotionally involved in the sessions. Moreover, medication can and usually does present side effects, especially when prescribed for a long period.

The sense of the physiological condition of the body, also referred to as interoception, is closely related to the experience of emotion. Studies of interoception and false autonomic feedback have a long history in Psychology.

False autonomic feedback consists of providing to a subject a modified or manipulated feedback regarding his/her current physiological condition, e.g. providing false cardiac or breathing activity information. The autonomic nervous system is a control system that acts largely unconsciously and regulates, among other, the heart rate, digestion, respiratory rate and pupillary response. Emotions are tightly linked to their autonomic representation. For this reason some autonomic patterns are enough to evoke the associated emotion. Therefore, autonomic feedback offers an alternative to therapy methods aiming at inducing or altering the emotions of a subject.

Virtual reality (VR) offers a variety of potential benefits for many aspects of rehabilitation assessment, treatment, and research. VR has the capacity to allow the creation and control of dynamic 3-dimensional (increased flexibility) environments, to provide extensive sensory feedback, plus ecologically valid stimulus in environments within which behavioral responding can be recorded and measured. Thus, VR offers clinical assessment and therapeutic options that are not available with traditional methods.

SUMMARY OF THE DISCLOSURE

According to a first aspect, a method for provoking a physiological response in a subject is provided. The method comprises substantially continuously receiving from one or more sensors an orientation of a head mounted display of the subject, substantially continuously receiving from one or more physiological sensors a measured parameter indicative of a physiological state of the subject, substantially continuously determining a video signal representing an avatar of the subject in a virtual reality scenario to be displayed on the head mounted display taking into account the orientation of the head mounted display, wherein the video signal includes an indication of a physiological state of the avatar, and sending the video signal to the head mounted display for visualization, wherein during a first period the indication of the physiological state of the avatar substantially corresponds to the measured physiological state of the subject, and during a second period the indication of the physiological state of the avatar does not correspond to the measured physiological state of the subject.

In examples according to this first aspect, a virtual treatment of a mental disorder of a subject can result in improved physiological and behavioural response, without the administration of medication and thus avoiding their side effects, and yielding a cost-effective alternative for therapy or rehabilitation.

A fully immersive virtual reality may be provided. As a subject moves his/her head, the video signal reproduced on the head mounted display is adapted to the real-time orientation of the head mounted display so that "ownership" of the virtual subject or avatar is achieved (i.e. the subject's brain is cheated into thinking that the virtual body belongs to the subject). This sense of ownership is further enhanced through the autonomic feedback, that is, the experience of the physiological state of the subject through the avatar.

Autonomic feedback does not necessarily need to be based on a realistic correspondence between the type of physiological response and what is displayed. In a realistic correspondence case, as one or more sensors measure, for instance, the real breathing or heart rate of the subject, the video signal reproduces them on the head mounted display by including an indication of such physiological state as of the avatar, namely through its chest movement or vibrations respectively, plus optionally the associated sounds. In an unrealistic case, e.g. heart beat might be represented by e.g. foot tapping, and blood pressure might be represented by the colour of the room—in which the virtual body is depicted.

During a second period of the treatment session, and prior to or during a stressful episode being played in the virtual reality environment, such physiological feedback is gradually manipulated so that the subject's brain continues to think that such physiological state corresponds to the actual condition of the subject. After a transitory period, during the second period of a session, the physiological feedback is correlated with the measured physiological state of the first period and the physiological state of the second period. Therefore during a stressful episode the subject might perceive his/her physiological feedback as that of a relaxed condition (e.g. slower heart rate) even though their true state initially has greater anxiety (faster heart rate). The goal is that the perceived lower heart rate would reduce the anxiety. Such a virtual treatment can improve the subject's response to stress (e.g. phobias) or train violent or overreactive subjects to relax when confronted with situations that can trigger their violent responses (e.g. a gender violence perpetrator, or a child abuser).

The present disclosure relates to a new method for the generation of false physiological feedback, through the exploitation of the concept of body ownership in immersive virtual reality. A virtual reality system according to the disclosure may enable participants to embody a virtual avatar and perceive their ongoing physiological activity through their virtual body representation. Patients may be endowed with life-sized virtual bodies that substitute their own body. The virtual body may be spatially coincident with the participants' real body, matching their posture and body movements, and it may be seen from a first person perspective. Respiration feedback can be displayed through the breathing motions of the virtual body. Heart rate feedback may be generated in real-time both acoustically and with vibrations over the heart area in the chest. Skin conductance or temperature feedback can also be displayed through a blushing or skin color change effect on the avatar. Thus, true (enhanced or not) physiological feedback can be generated with this method and it can also be used to generate false feedback.

An aim of the method is to show how manipulated physiological feedback provided through virtual embodiment may modulate the emotional appraisal and experience of situations, and physiological responses. In this sense, the method aims at providing a tool for individuals with mental disorders, who may suffer, inter alia, from emotional and/or behavioral problems, including lack of empathy and aggressive conducts, or anxiety disorders including phobias or obsessive compulsive disorder.

Advantageously the present method incorporates:
- the use of the real and ongoing physiological activity to provide the feedback;
- physiological measures such as respiration; and
- the quantification of the effects of both affective and physiological responses.

In examples, the present method offers promising potential for application in areas such as exposure therapies, to dampen the extreme reactions to a stressful situation, or alternatively to exaggerate the same to increase the feeling that events taking place in the virtual environment are "real" (plausibility); and the study of emotion, to incorporate manipulated physiological feedback of other measures not widely explored before.

In some examples, the method may comprise sending a signal to a tactile feedback device. The moment of tactile feedback may be correlated to or synchronised with the virtual feedback on the subject's heart rate, or with the virtual touch to the subject by another avatar or object within the virtual environment. Such a multisensory feedback increases a feeling of ownership in the subject, which reinforces the influence over the subject's brain plasticity and thus improves the method's results. The tactile feedback device may e.g. include one or more vibrators coupled to the chest or other parts of the body. The vibration of the vibrator coupled to the chest might be synchronised with the heart rate (according to the virtual feedback). In a visuomotor method, the feeling of ownership over the virtual body may be enhanced by the virtual body moving in synchrony with the real body. This is possible if there is motion capture with e.g. a motion sensing input device.

In another aspect, a computing system comprising a memory and a processor, wherein the memory stores computer program instructions executable by the processor is disclosed. The instructions may comprise the functionality to execute a method of providing a behavior therapy according to any of the examples disclosed herein.

In yet another aspect, a system for providing a treatment session for behavior therapy of a subject may comprise a computing system as above, a head-mounted display configured to reproduce a video signal received from the computing system, and one or more sensors configured to measure an orientation of a head mounted display of the subject and one or more physiological sensors for measuring the physiological state of the subject.

In some examples, the sensors configured to measure an orientation of a head mounted display may comprise accelerometers attached to, integrated in or coupled with the head mounted display. In other examples, the sensors may comprise video cameras. Software for object recognition and motion capture hardware can be used to determine movements of the subject and/or the head mounted display. In yet further examples, further sensors involving e.g. emitters and receivers, from which the position and orientation of the subject or the head mounted display may be derived from triangulation. In yet further examples, the sensors may include a geomagnetic field sensor integrated in the head mounted display.

In the examples disclosed herein, many different suitable head mounted displays could be used. For example, a Smartphone or tablet incorporated in a head mount may serve as the head mounted display.

In some examples, the physiological sensors configured to measure the physiological state of the subject may comprise skin conductance sensors, a heart rate monitor, a thermometer, a respiration sensor, and a blood pressure meter. Several of these may be combined in a new generation of devices such as smart phones or smart watches. These sensors may be located in different parts of the body and be connected to the computing system. A software for the virtual environment configuration may determine an association between changes on the physiological activity and changes in the avatar, that can be visualized on the head mounted display.

In some examples, the system may further comprise headphones. The computing system in such cases may send suitable audio signals for reproduction by the headphones. Through the headphones, the subject may hear a real or manipulated heartbeat sound corresponding to the physiological feedback. For instance, the sound may be similar to hearing the heart through a stethoscope.

In yet another aspect, a computer program comprising program instructions to carry out any of the methods for provoking a physiological response in a subject herein explained is disclosed. The computer program product may be embodied on a computer readable medium and may comprise instructions to provoke that a controller device implements a method of providing a behavior therapy to a subject according to examples disclosed herein.

The computer program product may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the processes. The carrier may be any entity or device capable of carrying the computer program. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

Additional objects, advantages and features of embodiments of the invention will become apparent to those skilled in the art upon examination of the description, or may be learned by practice of the invention.

BRIEF DESCRIPTION OF THE DRAWINGS

Non-limiting examples of the present disclosure will be described in the following, with reference to the appended drawings, in which.

DETAILED DESCRIPTION

Figure 1:
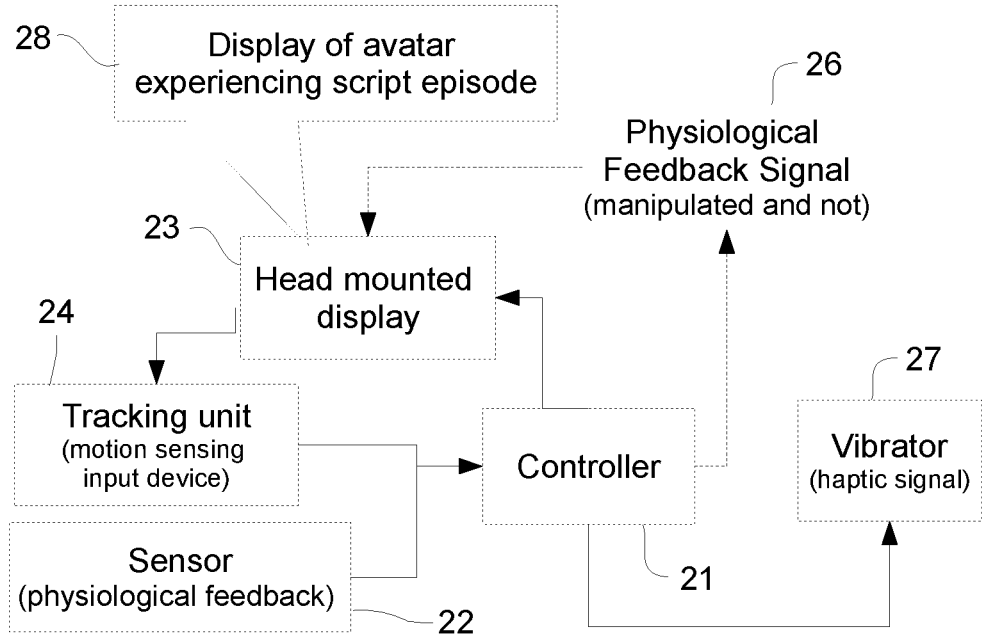
FIG. 1 illustrates a block diagram of an example of a system for providing behavior therapy of a subject.

FIG. 1 illustrates a block diagram describing an example of a system for providing behavior therapy of a subject. The system comprises a computing system of controller 21 connected to a head mounted display 23, a tracking unit 24, a sensor 22, a physiological feedback signal 26 and a vibrator 27.

The head mounted display 23 (HMD) may take many suitable shapes and forms. As mentioned before, it may consist of a mobile phone or Smartphone or tablet arranged in some form of head mount. Notably, there is no need for significant computing power in the HMD. The computing power may be provided in the actual HMD, but in some examples, the computing system may be physically separate from the HMD. The computing system in these cases may have a wireless connection with the HMD or may have a cable connection.

The tracking unit may include a plurality of sensors that in particular may determine the orientation and also the position of the head mounted display. From these sensors, the point of view and direction of view of the patient may be determined and this information is used to calculate the appropriate video signal corresponding to what the patient would see in the real world. The video signal may be determined by the computing system and communicated to the head mounted display. The display can reproduce the received signal and the patient will thus see the real-life situation but in the virtual reality, which can be accompanied by an audio signal and/or tactile stimulus synchronised with the display. A fully immersive virtual reality experience can thus be created.

The sense of embodiment may be defined as consisting of three subcomponents: the sense of self-location, the sense of agency, and the sense of body ownership. Embodiment is an important element for the system to achieve good results, because it basically means that the brain is deceived by the virtual reality environment, i.e., it believes that the virtual body is his/her own body, and responds to the virtually modified autonomic responses by stimulating neurocognitive connections so that the overall physiological and emotional/behavior response to certain situations, e.g. stressful situations, may be improved. For instance, it may enhance calming down in such stressful situations.

Various kinds of sensors and combinations of sensors can be used. For example, cameras can be used to determine the orientation of the head mounted display, and can also determine movements of e.g. body parts of the subject so that these movements can also be included in the video signal.

Such cameras may be combined for example with accelerometers integrated in the head mounted display and/or accelerometers attached to the patient.

On the display an avatar representing a subject in a virtual situation or in a virtual scenario is visualized. During this visualization, the physiological state parameters of the avatar are manipulated on the base of the measured values, and the avatar shows such changes in the display. The patient's brain can thus be cheated into thinking that the patient is actually experiencing the avatar's physiological state changes.

Physiological sensors for measuring the physiological state of the patient comprise: skin conductance sensors to measure perspiration (sweating), a heart rate monitor to measure pulse, a thermometer for temperature, a respiration sensor to measure the breathing rhythm, and a blood pressure meter.

Moreover, in some examples, a multisensory feedback may be provided. Said multisensory feedback signal may comprise a tactile feedback provided by a vibrator 27 in synchronization with the video signal of a 3D body representation display. The vibrator may be connected by cable or wirelessly with the controller 21. The controller may thus generate at a suitable moment a signal to active the vibrator 27. More than one vibrator could be used.

As mentioned above, when a vibration occurs in concurrence with or correlated to a virtual body heart rate feedback (in the case of a vibrator located on the chest of the subject), or to a virtual scenario contact by the other avatar or by any object in the scene of the script (in the case of vibrators located on body parts of the subject), the sense of ownership of the subject regarding the virtual body and his autonomic condition is enhanced.

There are a variety of ways in which such vibrating devices or alternative feedback devices may be used. In an example, if the script comprises a scene in which the subject touches or is being touched by a virtual object in the virtual reality, at the moment the avatar touches or is touched by the object, a tactile feedback may be created.

In some examples, headphones may be provided. The headphones may again be connected to the controller 21 (either wireless or otherwise). Through the headphones, a patient may hear the heartbeat corresponding to the virtual heartbeat feedback 26, be it the real (measured one) or the manipulated one (faster or slower corresponding to an aroused or relaxed state respectively), thus reinforcing the sense of ownership of the subject towards the avatar.

Figure 2:
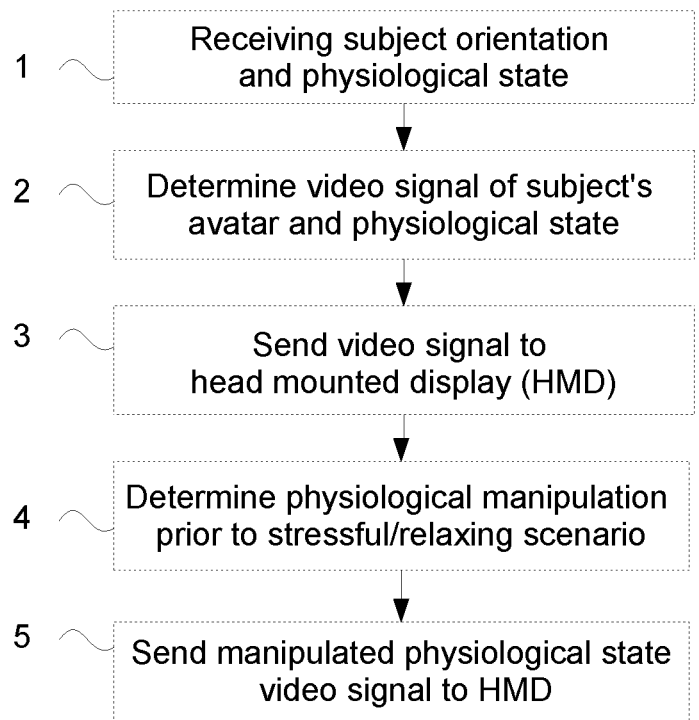
FIG. 2 illustrates a flow diagram of an example of a method as processed by the controller.

Referring to FIG. 2, a flow diagram describing an example of a method for behavior therapy of a subject is depicted, including the various steps of the method as processed by the controller.

At block 1, the controller 21 receiving a subject's orientation and physiological state may be provided. As mentioned above, the subject's orientation is measured by one or more sensors comprised in a motion sensing input device 24 which may in some examples be located on a head mounted display 23. Apart from the orientation of the HMD, also its position may be monitored and the position may be taken into account for the video signal to be generated. For example, if a subject moves his/her head forward or rearward without significantly affecting an HMD's orientation, the video signal to be reproduced may still be changed. Moreover, the physiological state of the subject is measured by one or more physiological sensors comprising skin conductance sensors, a heart rate monitor, a thermometer, a respiration sensor and/or a blood pressure meter. These values are thus monitored and thus the video signal may reproduce them according to the subject's state.

At block 2, the controller may determine a video signal which represents an avatar of the subject, i.e, the graphical representation of the subject undergoing the behaviour therapy, so that it may be displayed on the head mounted display 23. There may be mainly two kinds of situations scripted, which are basically the subject experiencing a particular situation and receiving a negative or stressful avatar feedback, and
    receiving a relaxing avatar feedback, with the target of inducing a feeling of stress or relaxation on the subject respectively.

Within the first type of situations scripted, the avatar may comprise a subject experiencing a stressful situation. For example, in cases where the subject is an abuser that victimizes other people, e.g. a male exerting domestic violence on his female partners in real life, the avatar might be a woman experiencing a gender violence episode in the virtual reality environment, so that the man sees himself but with the body of a woman, that moves as he moves. This is intended to cause the subject to develop empathy towards the victim, so that the aggressive behaviour is reduced after the therapy. The man can then receive a false feedback, e.g. a heart rate or respiration rate that is higher than the subject's real feedback. This can increase the stress of the subject as a victim and thereby increase the subject's empathy towards his victim/s by perceiving the aggression from their point of view along with their own stress.

In other cases falling within the second type of situations, for example the previous subject that mistreats women, the avatar might be a man in the virtual reality environment, experiencing an episode of interaction with a virtual woman. The virtual woman would behave in ways that typically trigger his violent reactions in real life. The man sees himself as the virtual man and receives a relaxing feedback from the avatar. This is intended to cause the subject to gain self-control in front of the victim's actions instead of overreacting, so that, again, the aggressive behaviour is reduced. Another example involving induction of relaxation may comprise a subject suffering from an anxiety disorder, e.g., a phobia such as fear of flying. The avatar might be a subject experiencing the situation that causes such anxiety or panic, i.e. the subject travelling by airplane. The video signal may take into account the orientation signal of the head mounted display and the body. Moreover, the video signal may include an indication of the physiological state of the avatar that substantially corresponds to the signal received at block 1 (i.e., the heart rate, perspiration, temperature, breathing and blood pressure values of the subject), so that it can induce a sense of ownership in the subject, which is particularly significant to increase the method's efficiency.

When a person experiences stress, fear or anger, an aroused physiological state develops, that is, heart rate (HR), breathing rhythm, perspiration (sweating), and blood pressure increase. By providing a feedback on the physiological condition of the body, not only ownership but also interoception of the virtual body are achieved. The latter, as mentioned above, has been closely related to the experience of emotion.

At block 3, the video signal may be sent to the head mounted display 23. During a first period of the treatment, as the subject perceives a real-time correspondence between the images seen on the display and his body's actual orientation in the environment, as well as his physiological condition at the time of visualization, his brain is led to assume the virtual body as his own, that is, to experience a sense of ownership of the virtual body.

At this point, physiological feedback of the respiratory and cardiac function may be manipulated. Thus, during a second period, the indication of the physiological state of the avatar does not correspond to the signal. Manipulation may be done in a progressive manner so that it goes unnoticed by the subject. This is further explained with reference to FIG. 4. Namely, fake respiratory feedback may be provided by the vision of respiratory movements seen on the virtual body, while cardiac feedback may be provided by a vibration on the chest plus the heartbeat sound. Aroused or relaxed physiological states may thus be provided through this setup.

Thereafter, at block 4, the subject may be exposed to a stimulus or experience that may be interpreted as stressful, according to a script episode. The script or screenplay may be adapted to the type of disorder that is to be treated.

The physiological feedback manipulation that may take place prior to this scene appearance may be calculated on the basis of a percentage change from each participant's own physiological activity. In order to ensure that the increase or decrease of the physiological activity is noticeable, a gradual manipulation may be used reaching 40% above or below the real one, ongoing physiological activity of the participant. The purpose of this is to act as a powerful biofeedback mechanism.

Advantageously, the degree of the virtual immersion, i.e., the intensity of the experience, may be adapted to the patient qualities and responses to previous treatment sessions. The method is therefore cost-effective compared to conventional treatments alternatives.

At block 5, said video signal may be sent to the head mounted display. The subject may thus see the avatar showing signs of the above described physiological state and the particular scenario, e.g. stressful or relaxing development according to the script.

Figure 3:
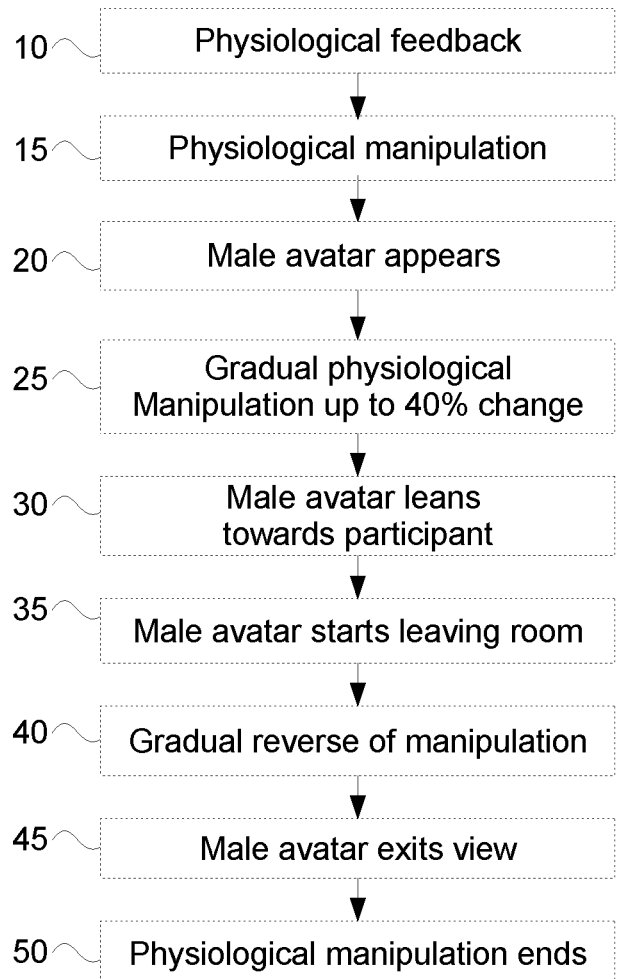
FIG. 3 illustrates a flow diagram of an example of a method for behavior therapy of a subject.

Referring to FIG. 3, a flow diagram of an example of an experiment for a method for behavior therapy of a subject is depicted. In this example, the subject may be a female who is put to face a situation involving a male's presence and action. A neutral interaction script might be at the core of the virtual reality immersion.

According to this example, at block 10, the video signal of the physiological state of the subject is reproduced so that the subject receives multisensory feedback on his/her current autonomic condition, so that a sense of ownership is achieved. The subject's avatar may be a woman.

At block 15, the manipulation of the physiological feedback may start. Fake respiratory, cardiac, perspiration or blood pressure feedback may be provided. An aroused physiological state may thus be provided to the subject.

Thereafter, at block 20, a male avatar appears and acts according to the script.

At block 25, a gradual manipulation may be used so that she experiences an aroused or relaxed state through an increase or decrease of the physiological activity.

At block 30, the male avatar may near the participant in a slightly circular approach, such that he comes up beside and just behind the woman's avatar. He may bend down into a crouch with his head at approximately the level of the woman's head and with a distance of approximately eighteen centimeters from the woman. The male avatar may remain in a crouched position for some time.

At block 45, a gradual reverse of the manipulation of the physiological state may start, and at block 50 the male avatar may stand up and walk back out of the environment.

Block 50 depicts the end of the physiological manipulation.

Although the script of this exercise is rather neutral, it has been found that, depending on the virtual feedback on physiological parameters given to a subject, a subject may experience more or less stress.

An example of a method for behavior therapy of a subject, comprising a similar structure to the example illustrated above, is described in the following. In this example, the patient may be a male subject who usually behaves violently against women. Thus, a gender violence related script might be at the core of the virtual reality immersion. Consequently, in such an example the subject's avatar may be a woman experiencing a gender violence episode in the virtual reality environment. The stressful experience might consist of being approached by a male avatar representing a potential attacker.

According to this example, the video signal of the physiological state of the subject is reproduced so that the subject receives multisensory feedback on his current autonomic condition. The subject's avatar in this case would preferably be a woman.

Afterwards, the manipulation of the physiological feedback may start. Fake respiratory, or cardiac, or perspiration or blood pressure feedback may be provided. An aroused physiological state may thus be provided to the subject. Thereafter, a male avatar appears, and a gradual manipulation may be used reaching 40% above the real physiological activity of the participant, so that he experiences an aroused state. The effect of such manipulation, e.g., of an increase of the physiological activity, may cause the subject to experience the (following) aggression episode from the victim's perspective. As previously explained, the result of such therapy may be developing empathy for the female victim.

In this case, the male avatar may come close to the participant and start attacking her psychologically, through insulting and humiliating wording or yelling. Then, a gradual reverse of the manipulation of the physiological state may start, and later on the male avatar may stand up and walk back out of the environment and the physiological manipulation ends.

As mentioned above, other applications may relate to anxiety or panic disorders, such as phobias. In such cases, the manipulation may consist of a decrease of the physiological activity prior to or in conjunction with a view of e.g. heights (for the treatment of acrophobia or fear of heights) or a flight simulation (for the treatment of fear of flying), so that the subject experiences a relaxed state associated with the feared object/situation.

The script contents may vary from one session to another, as well as the duration of the several steps may vary for a same script. The flexibility of the method allows the therapy to be adapted not only to several disorders but also to each patient and his/her therapy developments.

Figure 4:
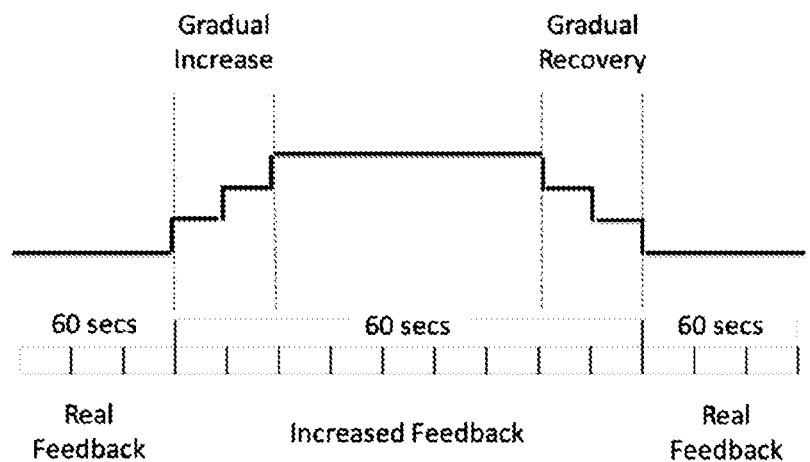
FIG. 4 illustrates schematically a diagram of the physiological feedback vs. time according to examples of the present method.

FIG. 4 schematically illustrates a diagram of the physiological feedback vs. time according to an example of the present method. The manipulation of the physiological feedback may in general have any duration. In this example, it has a total duration of 60 seconds, but this could be freely varied. The first time period may be used to gradually achieve the total percentage of manipulation in 3 steps. For example, the heart beat represented first corresponds to a subject's actual heart beat. The following transitory period may provide a constant continuous manipulation at the maximal magnitude, ±30 or 40%. For example, the depicted heart beat may be raised in steps: first, the heart rate is the actual heartbeat+10%, then the heart rate is the actual heart rate+20%, and then the heart rate is the actual heart rate+30%. A similar decrease may take place after a certain exercise. Preferably, the feedback provides a progressive change of the manipulated parameters, so that such change is consciously unnoticed by the subject.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. A method for provoking a physiological response in a subject during a session, the method comprising:
   receiving from one or more sensors an orientation of a head mounted device of the subject;
   receiving from one or more physiological sensors a measured parameter indicative of a physiological state of the subject;
   producing a video signal including an avatar representing the subject in a virtual reality scenario to be exhibited on a video display of the head mounted device taking into account the orientation of the head mounted device, wherein the video signal includes an indication of a first physiological state of the avatar and an indication of a second physiological state of the avatar, the virtual reality scenario including a stressful episode for the subject;
   sending the video signal to the head mounted device to produce on the video display of the head mounted device the avatar of the subject in the virtual reality scenario, wherein
   during a first period of the session the video signal includes the indication of the first physiological state of the avatar, the indication of the first physiological state of the avatar corresponding to the physiological state of the subject determined from the measured parameter;
   during a second period of the session the video signal includes the indication of the second physiological state of the avatar, the indication of the second physiological state of the avatar
   corresponding to a parameter having a value that is greater than or less than between 10% to 40% of a value of the measured parameter indicative of the physiological state of the subject, the second period of the session occurring after the first period of the session, in the second period of the session, the video signal includes the virtual reality scenario that includes the stressful episode; and
   there existing a transitory period between the first period of the session and the second period of the session during which the indication of the first physiological state of the avatar gradually changes to the indication of the second physiological state of the avatar.

2. The method according to claim 1, wherein the measured parameter comprises a heart rate.

3. The method according to claim 1, further comprising generating an audio signal simulating a heartbeat of the subject, and sending the audio signal to a device configured to reproduce the audio signal.

4. The method according to claim 1, further comprising continuously receiving from the one or more sensors, movements carried out by one or more body parts of the subject, and continuously producing the video signal representing the avatar of the subject in the virtual reality scenario to be exhibited on the video display taking into account the orientation of the head mounted device and the movements of the one or more body parts.

5. The method according to claim 1, wherein the step of receiving from the one or more sensors the orientation of the head mounted device of the subject occurs continuously; the step of receiving from the one or more physiological sensors the measured parameter indicative of the physiological state of the subject occurs continuously; and the step of producing the video signal occurs continuously.

6. The method according to claim 1, wherein the measured parameter indicative of the physiological state of the subject comprises a respiration rate.

7. The method according to claim 1, wherein the measured parameter indicative of the physiological state of the subject comprises a skin temperature.

8. A computing system comprising a memory and a processor, wherein the memory stores computer program instructions executable by the processor, said instructions comprising functionality to execute a method of providing a behavior therapy, wherein the method comprises:
receiving from one or more sensors an orientation of a head mounted device of a subject;
receiving from one or more physiological sensors a measured parameter indicative of a physiological state of the subject;
producing a video signal including an avatar representing the subject in a virtual reality scenario to be exhibited on a video display of the head mounted device taking into account the orientation of the head mounted device, wherein the video signal includes an indication of a first physiological state of the avatar and an indication of a second physiological state of the avatar, the virtual reality scenario including a stressful episode for the subject;
sending the video signal to the head mounted device to produce on the video display of the head mounted device the avatar of the subject in the virtual reality scenario, wherein
during a first period of the session the video signal includes the indication of the first physiological state of the avatar, the indication of the first physiological state of the avatar corresponding to the physiological state of the subject determined from the measured parameter;
during a second period of the session the video signal includes the indication of the second physiological state of the avatar, the indication of the second physiological state of the avatar corresponding to a parameter having a value that is greater than or less than between 10% to 40% of a value of the measured parameter indicative of the physiological state of the subject, the second period of the session occurring after the first period of the session, in the second period of the session, the video signal includes the virtual reality scenario that includes the stressful episode; and
there existing a transitory period between the first period of the session and the second period of the session during which the indication of the first physiological state of the avatar gradually changes to the indication of the second physiological state of the avatar.

9. A system for providing a treatment session for the behavior therapy of the subject, the system comprising: the computing system according to claim 8;
the head mounted device having the video display and configured to receive the video signal from the computing system; the one or more sensors configured to measure the orientation of the head mounted device, and the one or more physiological sensors for measuring the physiological state of the subject.

10. The system according to claim 9, wherein the system further comprises headphones configured to reproduce an audio signal received from the computing system.

11. The system according to claim 10, wherein the audio signal is an audio signal simulating a heartbeat of the subject.

12. The system according to claim 9, wherein the one or more sensors configured to measure the orientation of the head mounted device is selected from the group consisting of accelerometers attached to the head mounted device and video cameras.

13. The system according to claim 9, wherein the system further comprises a tactile feedback device for providing a tactile feedback to the subject in response to a signal received from the computing system.

14. The system according to claim 13, wherein the tactile feedback device is a vibrator.

15. The system according to claim 9, wherein the one or more physiological sensors include a heart rate monitor to measure a pulse of the subject.

16. The system according to claim 9, wherein the one or more physiological sensors include a respiration sensor to measure a breathing rhythm of the subject.

17. The system according to claim 9, wherein the one or more physiological sensors include a skin conductance sensor to measure perspiration of the subject.

18. The system according to claim 9, wherein the one or more physiological sensors include a thermometer for measuring a skin temperature of the subject.

* * * * *